(12) United States Patent
Druma

(10) Patent No.: US 10,398,484 B2
(45) Date of Patent: Sep. 3, 2019

(54) INFLATABLE BONE TAMP WITH FLOW CONTROL AND METHODS OF USE

(71) Applicant: Medtronic Holding Company Sàrl, Tolochenaz (CH)

(72) Inventor: Calin Druma, San Jose, CA (US)

(73) Assignee: Medtronic Holding Company Sàrl, Tolochenaz (CH)

(*) Notice: Subject to any disclaimer, the term of this patent is extended or adjusted under 35 U.S.C. 154(b) by 293 days.

(21) Appl. No.: 15/189,787

(22) Filed: Jun. 22, 2016

(65) Prior Publication Data

US 2017/0367747 A1 Dec. 28, 2017

(51) Int. Cl.
*A61B 17/88* (2006.01)

(52) U.S. Cl.
CPC ...... *A61B 17/8855* (2013.01); *A61B 17/8827* (2013.01)

(58) Field of Classification Search
CPC .................................................. A61B 17/8855
See application file for complete search history.

(56) References Cited

U.S. PATENT DOCUMENTS

| 3,211,150 | A | 10/1965 | Foderick |
| 6,911,038 | B2* | 6/2005 | Mertens ................ A61F 2/958 |
| | | | 606/192 |
| 7,261,720 | B2 | 8/2007 | Stevens et al. |
| 8,241,335 | B2 | 8/2012 | Truckai et al. |
| 2004/0186471 | A1 | 9/2004 | Trieu |
| 2009/0299327 | A1* | 12/2009 | Tilson ................ A61B 17/8816 |
| | | | 604/500 |
| 2012/0165941 | A1* | 6/2012 | Rabiner ............. A61B 17/7097 |
| | | | 623/17.12 |
| 2013/0237950 | A1* | 9/2013 | Gianotti ................. A61F 2/958 |
| | | | 604/500 |
| 2013/0238038 | A1 | 9/2013 | Auyoung |
| 2013/0261729 | A1 | 10/2013 | Gillick et al. |
| 2014/0128877 | A1* | 5/2014 | O'Halloran ........ A61B 17/1617 |
| | | | 606/94 |
| 2014/0276572 | A1 | 9/2014 | Auyoung et al. |
| 2014/0303730 | A1 | 10/2014 | McGuire et al. |
| 2015/0342660 | A1 | 12/2015 | Nash |

FOREIGN PATENT DOCUMENTS

| EP | 1313411 B1 | 10/2007 |
| WO | 0217801 A2 | 3/2002 |
| WO | 0217801 A3 | 3/2002 |
| WO | 2013074933 A1 | 5/2013 |

OTHER PUBLICATIONS

European Search Report and Opinion for EP17177266 the counterpart application dated Nov. 16, 2017, 9 pages.

* cited by examiner

*Primary Examiner* — Olivia C Chang

(57) ABSTRACT

An inflatable bone tamp is provided that includes a shaft defining a lumen. A balloon is coupled to the shaft such that a material can flow through the lumen and into the balloon to inflate the balloon. A connector is coupled to the shaft. The connector includes a first port and a second port. The ports are in communication with the lumen. A flow control device is coupled to the first port. The flow control device controls flow of the material through the first port and into the lumen. A damper is coupled to the second port. The damper controls pressure within the inflatable bone tamp when pressure within the inflatable bone tamp reaches a threshold. Kits, systems and methods are disclosed.

20 Claims, 6 Drawing Sheets

INFLATABLE BONE TAMP WITH FLOW CONTROL AND METHODS OF USE

TECHNICAL FIELD

The present disclosure generally relates to medical devices for the treatment of bone disorders, and more particularly to devices and methods for treating spinal disorders, such as, for example, vertebral compression fractures.

BACKGROUND

Height loss is commonly associated with spinal fractures, such as, for example, vertebral compression fractures. Spinal fractures affect a large segment of osteoporotic patients. It is estimated that approximately 700,000 spinal fractures occur annually from osteoporosis, for example. Procedures have been developed to treat spinal fractures. One such procedure is kyphoplasty. Kyphoplasty is a minimally invasive procedure that is used to treat spinal fractures, such as, for example, vertebral compression fractures by inserting one or more balloons, such as, for example, compliant balloons inside a fractured vertebral body. The balloon or balloons are inflated within the fractured vertebral body such that the cancellous bone of the vertebral body is pushed towards cortical walls of the vertebral body to form a cavity within the vertebral body. The cavity is then at least partially filled with a material, such as, for example, bone cement.

However, conventional spinal fracture treatment procedures lack a means to control the inflation rate of the balloon or balloons. This may lead to uneven inflation, balloon ruptures, or suboptimal balloon performance. To achieve optimal results, there is a need to provide a balloon or balloons that are inflated slowly to allow the balloon or balloons to gradually compress bone and restore height to the vertebral body. Bone is a viscoplastic material that needs time to deform. Fast inflation does not allow the balloon to create a large cavity. Conventional spinal fracture treatment procedures rely on the physician to control the inflation rate of the balloon or balloons. Inflating at a lower rate is not typically desired because it leads to a longer procedure time. However, providing a more steady and uniform inflation rate as described herein will lead to better and more predictable patient outcomes.

SUMMARY

New devices and methods are provided for the treatment of bone disorders, and more particularly devices and methods for treating spinal disorders, such as, for example, vertebral compression fractures. In some embodiments, the devices comprise an inflatable bone tamp (IBT) that includes a shaft defining a lumen. A balloon is coupled to the shaft such that a material can flow through the lumen and into the balloon to inflate the balloon. A connector is coupled to the shaft. The connector includes a first port and a second port. The ports are in communication with the lumen. A flow control device is coupled to the first port. The flow control device controls flow of the material through the first port and into the lumen. A damper is coupled to the second port. The damper controls pressure within the inflatable bone tamp when pressure within the inflatable bone tamp reaches a threshold.

Additional features and advantages of various embodiments will be set forth in part in the description that follows, and in part will be apparent from the description, or may be learned by practice of various embodiments. The objectives and other advantages of various embodiments will be realized and attained by means of the elements and combinations particularly pointed out in the description and appended claims.

BRIEF DESCRIPTION OF THE DRAWINGS

The present disclosure will become more readily apparent from the specific description accompanied by the following drawings, in which.

DETAILED DESCRIPTION

Figure 1:
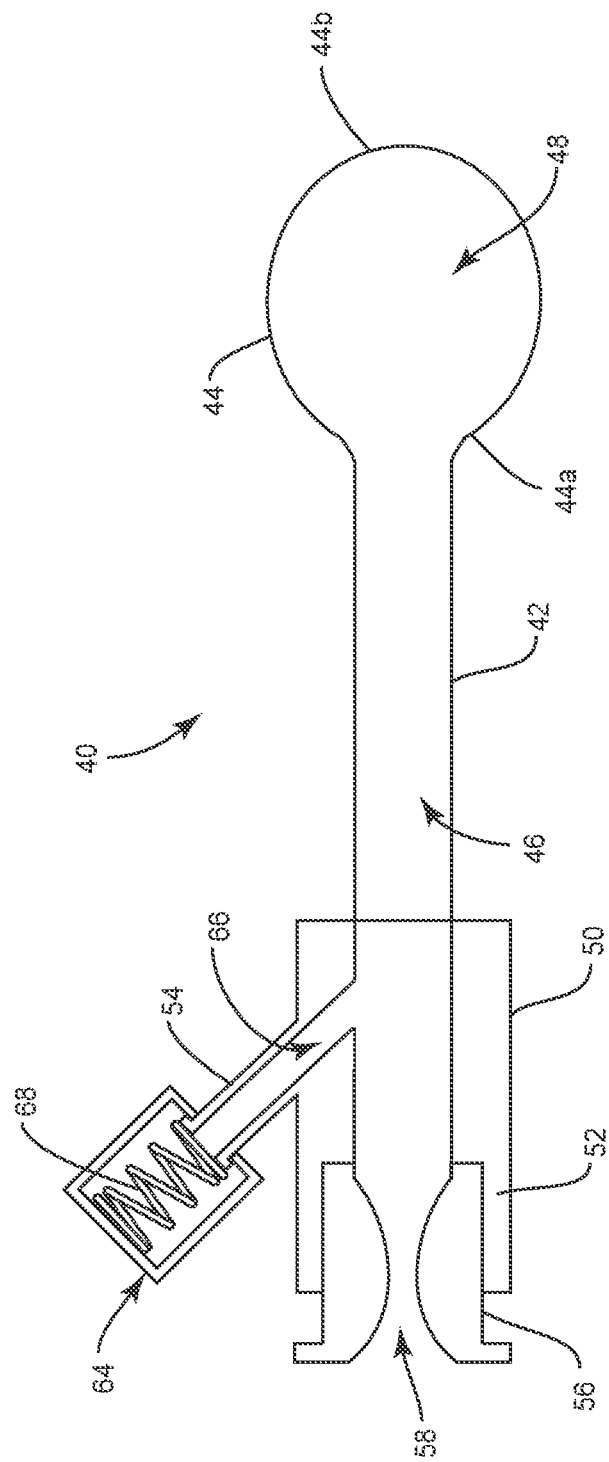
FIG. 1 is a side, cross sectional view of components of a surgical instrument in accordance with the principles of the present disclosure.

For the purposes of this specification and appended claims, unless otherwise indicated, all numbers expressing quantities of ingredients, percentages or proportions of materials, and other numerical values used in the specification and claims, are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding the numerical ranges and parameters set forth herein, the broad scope of the invention are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all subranges subsumed therein. For example, a range of "1 to 10" comprises any and all subranges between (and including) the minimum value of 1 and the maximum value of 10, that is, any and all subranges having a minimum value of equal to or greater than 1 and a maximum value of equal to or less than 10, e.g., 5.5 to 10.

Reference will now be made in detail to certain embodiments of the invention, examples of which are illustrated in the accompanying drawings. While the invention will be described in conjunction with the illustrated embodiments, it will be understood that they are not intended to limit the invention to those embodiments. On the contrary, the invention is intended to cover all alternatives, modifications, and equivalents that may be comprised within the invention as defined by the appended claims.

This disclosure is directed to an inflatable bone tamp, such as, for example, a balloon catheter 40. In some embodiments, the components of balloon catheter 40 can be fabricated from biologically acceptable materials suitable for medical applications, including metals, synthetic polymers, ceramics and bone material and/or their composites, depending on the particular application and/or preference of a medical practitioner. For example, the components of balloon catheter 40, individually or collectively, can be fabricated from materials such as stainless steel alloys, commercially pure titanium, titanium alloys, Grade 5 titanium, super-elastic titanium alloys, cobalt-chrome alloys, stainless steel alloys, superelastic metallic alloys (e.g., Nitinol, super elasto-plastic metals, such as GUM METAL® manufactured by Toyota Material Incorporated of Japan), ceramics and composites thereof such as calcium phosphate (e.g., SKEL-ITE™ manufactured by Biologix Inc.), thermoplastics such as polyaryletherketone (PAEK) including polyetheretherketone (PEEK), polyetherketoneketone (PEKK) and polyetherketone (PEK), carbon-PEEK composites, PEEK-BaSO$_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate, tri-calcium phosphate (TCP), hydroxyapatite (HA)-TCP, calcium sulfate, or other resorbable polymers such as polyaetide, polyglycolide, polytyrosine carbonate, polycaroplaetohe and their combinations.

Various components of balloon catheter 40 may have material composites, including the above materials, to achieve various desired characteristics such as strength, rigidity, elasticity, compliance, biomechanical performance, durability and radiolucency or imaging preference. The components of balloon catheter 40, individually or collectively, may also be fabricated from a heterogeneous material such as a combination of two or more of the above-described materials. The components of balloon catheter 40 may be monolithically formed, integrally connected or comprise fastening elements and/or instruments, as described herein.

Balloon catheter 40 comprises an outer shaft or cannula, such as, for example, cylindrical portion 42 and a balloon 44 coupled to cylindrical portion 42. In the embodiments shown in FIGS. 1 and 2, a proximal portion 44a of balloon 44 is coupled to cylindrical portion 42 and an opposite distal portion 44b of balloon 44 is spaced apart from or nonadjacent to the cylindrical portion 42. Cylindrical portion 42 is hollow and defines a passageway 46. In some embodiments, passageway 46 is in communication with an internal chamber 48 of balloon 44. In some embodiments, passageway 46 is configured to for passage of a material to move balloon 44 from an unexpanded configuration, such as, for example, an uninflated configuration to an expanded configuration, such as, for example, an inflated configuration. That is, a material may be moved through lumen or passageway 46 and into chamber 48 to move balloon 44 from the uninflated configuration to the inflated configuration. In some embodiments, when balloon 44 is in the inflated configuration, balloon 44 has a maximum diameter that is greater than the maximum diameter of balloon 44 when balloon 44 is in the uninflated configuration. That is, balloon 44 expands radially as balloon 44 moves from the uninflated configuration to the inflated configuration. In some embodiments, when balloon 44 is in the inflated configuration, balloon 44 has a maximum length that is greater than the maximum length of balloon 44 when balloon 44 is in the uninflated configuration. That is, balloon 44 expands longitudinally as balloon 44 moves from the uninflated configuration to the inflated configuration. In some embodiments, the material is a liquid, such as, for example, a contrast solution, saline or water. In some embodiments, passageway 46 is configured for passage of a material to move balloon 44 from the inflated configuration to the uninflated configuration, as discussed herein. That is, the material moves through passageway 46 and out of balloon catheter 40 to allow balloon 44 to deflate.

In some embodiments, cylindrical portion 42 is a hollow shaft or tube. In some embodiments, cylindrical portion 42 is flexible to allow cylindrical portion 42 to bend as cylindrical portion 42 is navigated through a patient's anatomy. For example, cylindrical portion 42 may be flexible to allow cylindrical portion 42 to be navigated along a curved path created by a medical practitioner in order to position balloon 44 at, in or near a target location or treatment zone, such as, for example, within a vertebral body. In embodiments wherein cylindrical portion 42 is flexible, cylindrical portion 42 can be bent without breaking cylindrical portion 42. In some embodiments, cylindrical portion 42 is rigid such that cylindrical portion 42 cannot be bent without cylindrical portion 42 breaking. For example, cylindrical portion 42 may be rigid to provide strength to cylindrical portion 42 in applications wherein balloon catheter 40 is navigated along a straight path created by a medical practitioner in order to position balloon 44 at, in or near a target location or treatment zone, such as, for example, a space within a vertebral body. In some embodiments, cylindrical portion 42 is a polymer tube.

In some embodiments, balloon 44 is made from a resilient biocompatible material. In one embodiment, balloon 44 is a compliant balloon that resists stretching. In one embodiment, balloon 44 comprises polyolefin copolymer (POC), Polyurethane, Nylon. In one embodiment, balloon 44 is a non-compliant or semi-compliant balloon that stretches, at least to some degree. In one embodiment, balloon 44 comprises polyethylene terapthelate (PET). In some embodiments, balloon 44 can have various cross section configurations when balloon 44 is in the inflated configuration, such as, for example, oval, oblong, triangular, rectangular, square, polygonal, irregular, uniform, non-uniform, variable, tubular and/or tapered. In some embodiments, an outer surface of balloon 44 may have various surface configurations, such as, for example, smooth and/or surface configurations to enhance fixation with tissue, such as, for example, rough, arcuate, undulating, porous, semi-porous, dimpled, polished and/or textured.

Balloon 44 can be a single or a multi-layered balloon, where each balloon layer has the same diameter and/or wall thickness, is comprised of the same material or materials having substantially identical mechanical properties, and has the same degree of molecular orientation in the body portion of the balloon. It will be apparent that in some situations it will be desirable to have some balloon layers having different thicknesses, materials, and/or degree of molecular orientations upon deflation, while at the same time having equivalent size, mechanical properties, and/or orientation upon inflation.

Figure 2:
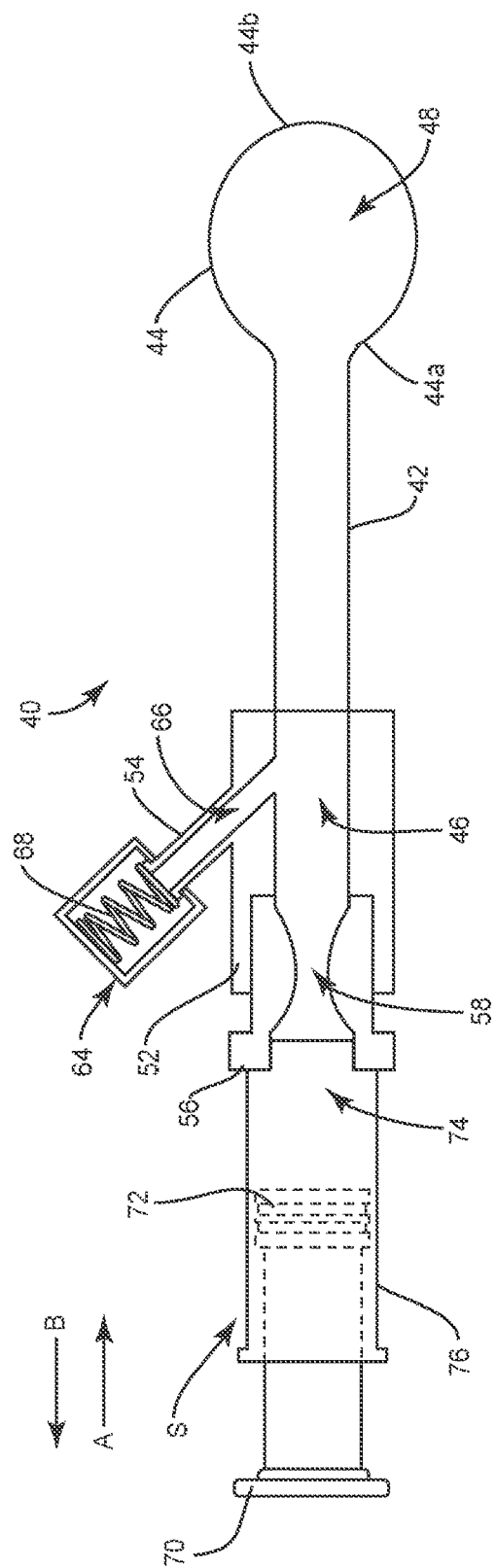
FIG. 2 is a side, cross sectional view of the surgical instrument shown in FIG. 1.

Balloon catheter 40 comprises a connector 50 that is coupled to cylindrical portion 42. Connector 50 comprises a port 52 and a port 54 that is spaced apart from port 52. One or more flow control devices, such as, for example, a flow control device 56 is coupled to port 52 such that a channel 58 of flow control device 56 is in communication with passageway 46. This allows an inflation device, such as, for example, a syringe S to be coupled to port 52 such that syringe S can inject a material through channel 58 and passageway 46 and into inner cavity 48 to move balloon 44 from the uninflated configuration to the inflated configuration. Flow control device is configured to restrict or otherwise limit the rate of flow of a material as the material flows through channel 58, as discussed herein. In some embodiments, channel 58 extends parallel and is coaxial with passageway 46, as shown in FIGS. 1 and 2. In some embodiments, channel 58 may be disposed at alternate orientations, relative to passageway 46, such as, for example, transverse, perpendicular and/or other angular orientations such as acute or obtuse and/or may be offset or staggered. In some embodiments, channel 58 may have various cross section configurations, such as, for example, oval, oblong, triangular, rectangular, square, polygonal, irregular, uniform, non-uniform, variable, tubular and/or tapered. In some embodiments, coupled to port 52 by frictional engagement, threaded engagement, mutual grooves, screws, adhesive, nails, barbs and/or raised element.

In some embodiments, flow control device 56 is integrally formed with connector 50 such that flow control device 56 cannot be removed from connector 50 without breaking connector 50 and/or flow control device 56. In some embodiments, flow control device 56 is removable from connector 50 to allow a medical practitioner to select between differently configured flow control devices that can be coupled to port 52. For example, the medical practitioner can select a flow control device, such as, for example, flow control device 56 from a plurality of flow control devices that each restrict or otherwise limit the rate of flow of a material as the material flows through channel 58 differently. For example, when a faster rate of flow is desired, the medical practitioner can select the flow control device that allows for a faster rate of flow. If, on the other hand, a slower rate of flow is desired, the medical practitioner can select the flow control device that allows for a slower rate of flow. The differently configured flow control devices may be part of a kit, which is within the scope of the present disclosure. In embodiments wherein flow control device 56 is removable from connector 50, flow control device 56 may be coupled to connector 50 by frictional engagement, threaded engagement, mutual grooves, screws, adhesive, nails, barbs and/or raised element.

In some embodiments, channel 58 is tapered to restrict or otherwise limit the rate of flow of a material as the material flows through channel 58 and into passageway 46. It is envisioned that this will slow the flow rate of the material as the material moves into interior cavity 48 of balloon 44 from passageway 46 to move balloon 44 from the uninflated configuration to the inflated configuration. That is, the flow rate of the material will be less when channel 58 is tapered than when channel is not tapered, such as, for example, when channel 58 has a uniform width or diameter.

Figure 1A:
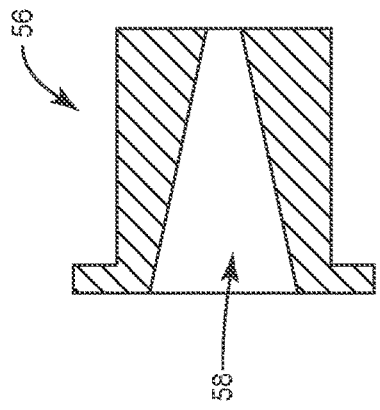
FIG. 1A is a side, cross sectional view of one embodiment of a component of the surgical instrument shown in FIG. 1 in accordance with the principles of the present disclosure.
Figure 1B:
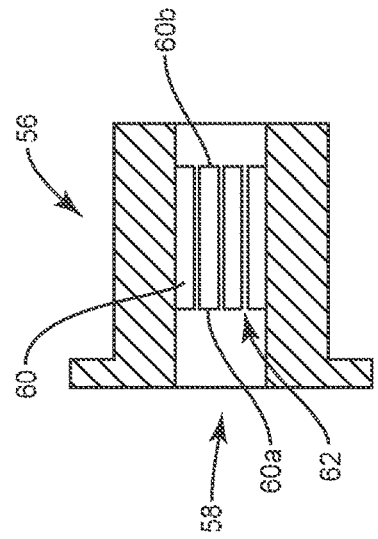
FIG. 1B is a side, cross sectional view of one embodiment of a component of the surgical instrument shown in FIG. 1 in accordance with the principles of the present disclosure.
Figure 1C:
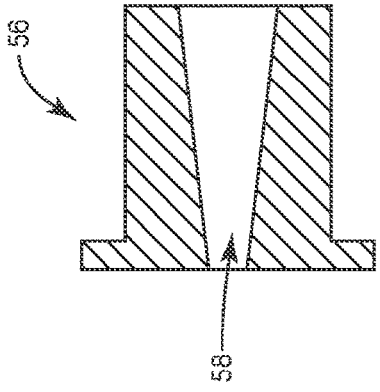
FIG. 1C is a side, cross sectional view of one embodiment of a component of the surgical instrument shown in FIG. 1 in accordance with the principles of the present disclosure.

Channel 58 can be tapered in different ways to restrict or otherwise limit the rate of flow of the material through channel 58. In some embodiments, flow control device 56 comprises a convexly curved inner surface such that channel 58 is tapered from a proximal end of flow control device 56 to a midpoint of flow control device 56 and from a distal end of flow control device 56 to the midpoint, as shown in FIGS. 1 and 2. In some embodiments, the inner surface is continuously curved from the proximal end of flow control device 56 to the midpoint of flow control device 56 and continuously curved from the distal end of flow control device 56 to the midpoint. In some embodiments, the inner surface has a continuous radius of curvature from the proximal end of flow control device 56 to the midpoint of flow control device 56 and a continuous radius of curvature from the distal end of flow control device 56 to the midpoint. In some embodiments, channel 58 is tapered from the distal end of flow control device 56 to the proximal end of flow control device 56, as shown in FIG. 1A. In some embodiments, channel 58 is tapered continuously from the proximal end of flow control device 56 to the distal end of flow control device 56. In some embodiments, channel 58 is tapered from a proximal end of flow control device 56 to the distal end of flow control device 56, as shown in FIG. 1B. In some embodiments, channel 58 is tapered continuously from the distal end of flow control device 56 to the proximal end of flow control device 56. In some embodiments, channel 58 includes a stepped configuration, as shown in FIG. 1C, such that the diameter of channel 58 decreases incrementally along the length of channel 58.

Figure 1D:
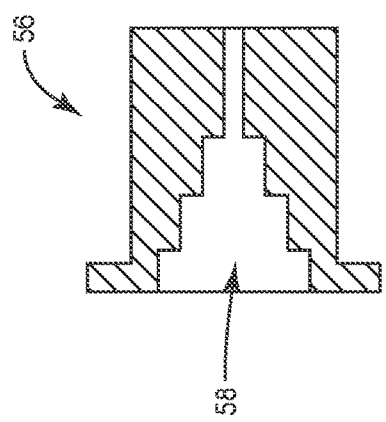
FIG. 1D is a side, cross sectional view of one embodiment of a component of the surgical instrument shown in FIG. 1 in accordance with the principles of the present disclosure.

In one embodiment, shown in FIG. 1D, flow control device 56 comprises a member 60 positioned within channel 58. Member 60 comprises one or a plurality of pores 62 that are in communication with channel 58 such that a material can move from an inflation device, such as, for example, syringe S, through pores 62 and into passageway 46. In some embodiments, member 60 is an open cell foam material or spongiform material/structure. In some embodiments, at least one of pores 62 extends through opposite proximal and distal surfaces 60a, 60b of a respective member 60. In some embodiments, at least one of pores 62 extends through one of proximal and distal surfaces 60a, 60b without extending through the other one of proximal and distal surfaces 60a, 60b. In some embodiments, at least one of pores 62 is in communication with at least another one of pores 62. In some embodiments, pores 62 are interconnected with one another. In some embodiments, pores 62 are spaced apart from nonadjacent to one another and/or are not in communication with one another.

One or more valves, such as, for example, a check valve or damper 64 is coupled to port 54. A cavity 66 of port 54 is in communication with passageway 46. Damper 64 is in communication with passageway or cavity 66 of port 54 such that damper 64 is affected by pressure within passageway 46. In some embodiments, damper 64 includes a biasing member, such as, for example, a coiled spring 68 that contracts or compresses in response to increased pressure within passageway 46 and expands in response to decreased pressure within passageway 46. The compression and expansion of spring 68 allows damper 64 to smoothen pressure peaks within passageway 46. As such, damper 46 can prevent pressure within passageway 46 from increasing too quickly, for example. That is, damper 46 takes the blunt force of the fast rising pressure within passageway 46. In some embodiments, damper 46 is configured such that spring 68 will compress only when pressure within passageway 46 reaches a certain threshold.

In some embodiments, balloon catheter 40 comprises a plurality of dampers, such as, for example, damper 64 that can each be removably coupled to port 54. In some embodiments, each of dampers 64 is configured such that springs 68 compress at a different threshold pressure. This allows a medical practitioner to select a damper 64 that works at a selected threshold pressure. In embodiments wherein dampers 64 are removable from connector 50, damper 64 may be coupled to port 54 by frictional engagement, threaded engagement, mutual grooves, screws, adhesive, nails, barbs and/or raised element.

In operation and use, an inflation device, such as, for example, syringe S is coupled to port 52. In some embodiments, a distal tip of syringe S is coupled to flow control device 56, as shown in FIG. 2. In some embodiments, the distal tip of syringe S includes outer threads that engage inner threads of flow control device 56 to couple syringe S to flow control device 56. A plunger 70 of syringe S is moved in direction A shown in FIG. 2 such that a tip 72 of plunger 70 pushes material, such as, for example, inflation material within a cavity 74 of a barrel 76 of syringe S out of cavity 74. The material moves out of syringe S and through channel 58 of flow control device 56. As the material moves through channel 58, the rate of flow of the material is reduced, as discussed herein. That is, the rate of flow of the material decreases within channel 58 from the rate of flow when the material exits syringe S. The material then flows through passageway 46 at the reduced rate of flow and into inner cavity 48 of balloon 44 to move balloon from the uninflated configuration to the inflated configuration. As the material flows through passageway 46, spring 68 of damper 66 will compress if pressure within passageway 46 reaches a certain threshold in order to smoothen pressure peaks within passageway 46, as discussed herein. In some embodiments, the material may be withdrawn from balloon 44 by moving plunger 70 in the direction shown by arrow B in FIG. 2. In particular, moving plunger 70 in the direction shown by arrow B creates pressure that draws the material out of inner cavity 48, through passageway 46 and channel 58 and into syringe S to move balloon 44 from the inflated configuration to the uninflated configuration.

In use, to treat a bone disorder, such as, for example, a spinal fracture, a medical practitioner obtains access to a target location including at least one vertebra, such as, for example, a fractured vertebra, in any appropriate manner, such as through incision and retraction of tissue. It is envisioned that the balloon catheter 40 may be used in any existing surgical method or technique including open surgery, mini-open surgery, minimally invasive surgery including percutaneous surgical implantation, whereby vertebra V is accessed through a micro-incision, or sleeve that provides a protected passageway to the area. Once access to the surgical site(s) are obtained, the particular surgical procedure is performed for treating the bone disorder.

Balloon catheter 40 is moved through the incision and positioned so that balloon 44 is positioned within a vertebral body of the fractured vertebra. In some embodiments, balloon 44 is moved into the vertebral body when balloon 44 is in the uninflated configuration. The material discussed above is moved through passageway 46 such that the material flows through passageway 46, channel 58 and into cavity 48 of balloon 44 to move balloon 44 from the uninflated configuration to the inflated configuration. As balloon 44 is gradually inflated, balloon 44 pushes cancellous bone of the vertebral body towards cortical walls of the vertebral body to form a cavity within the vertebral body. In some embodiments, the cavity created by balloon 44 is filled with a material, such as, for example, bone cement.

Figure 3:
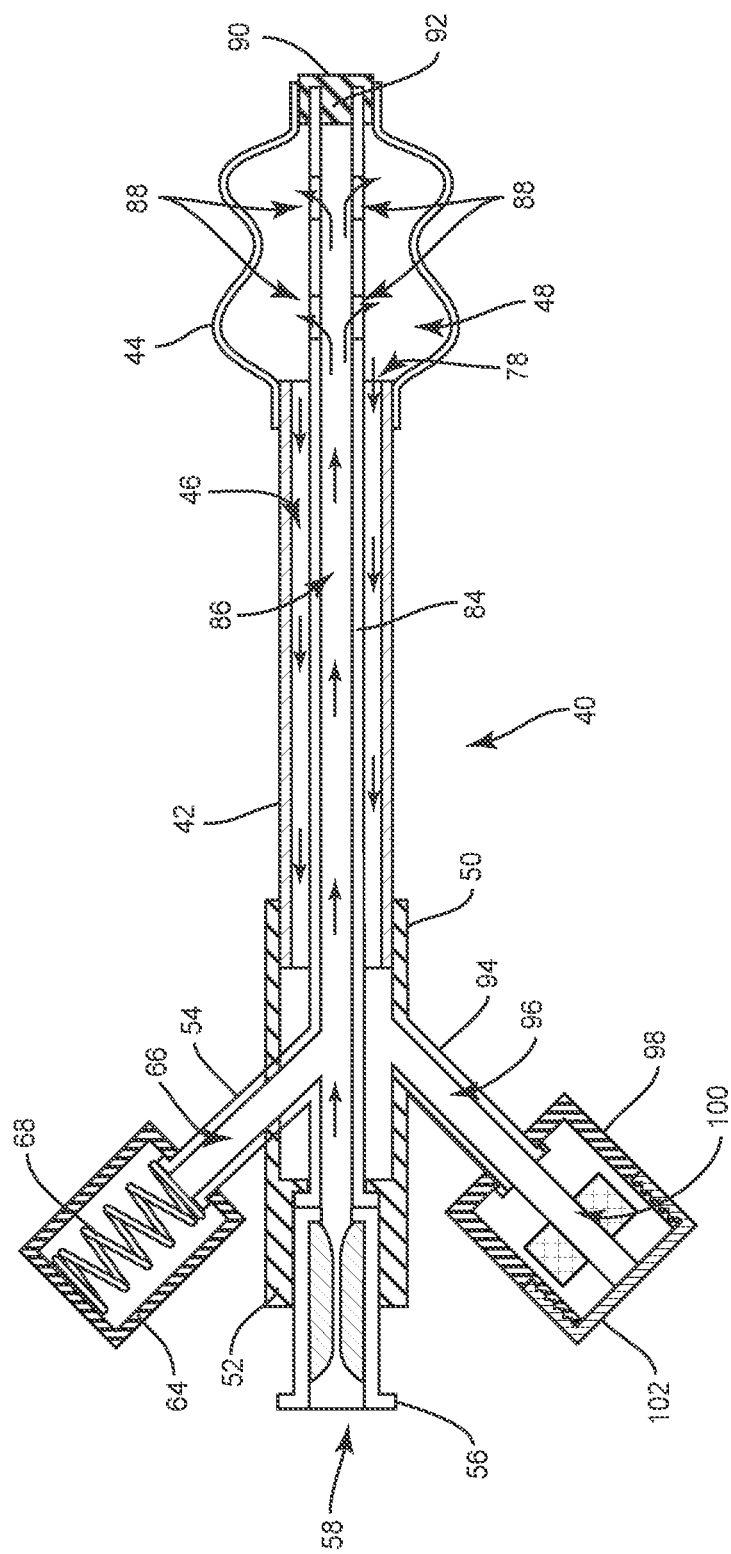
FIG. 3 is a side, cross sectional view of components of a surgical instrument in accordance with the principles of the present disclosure.
Figure 4:
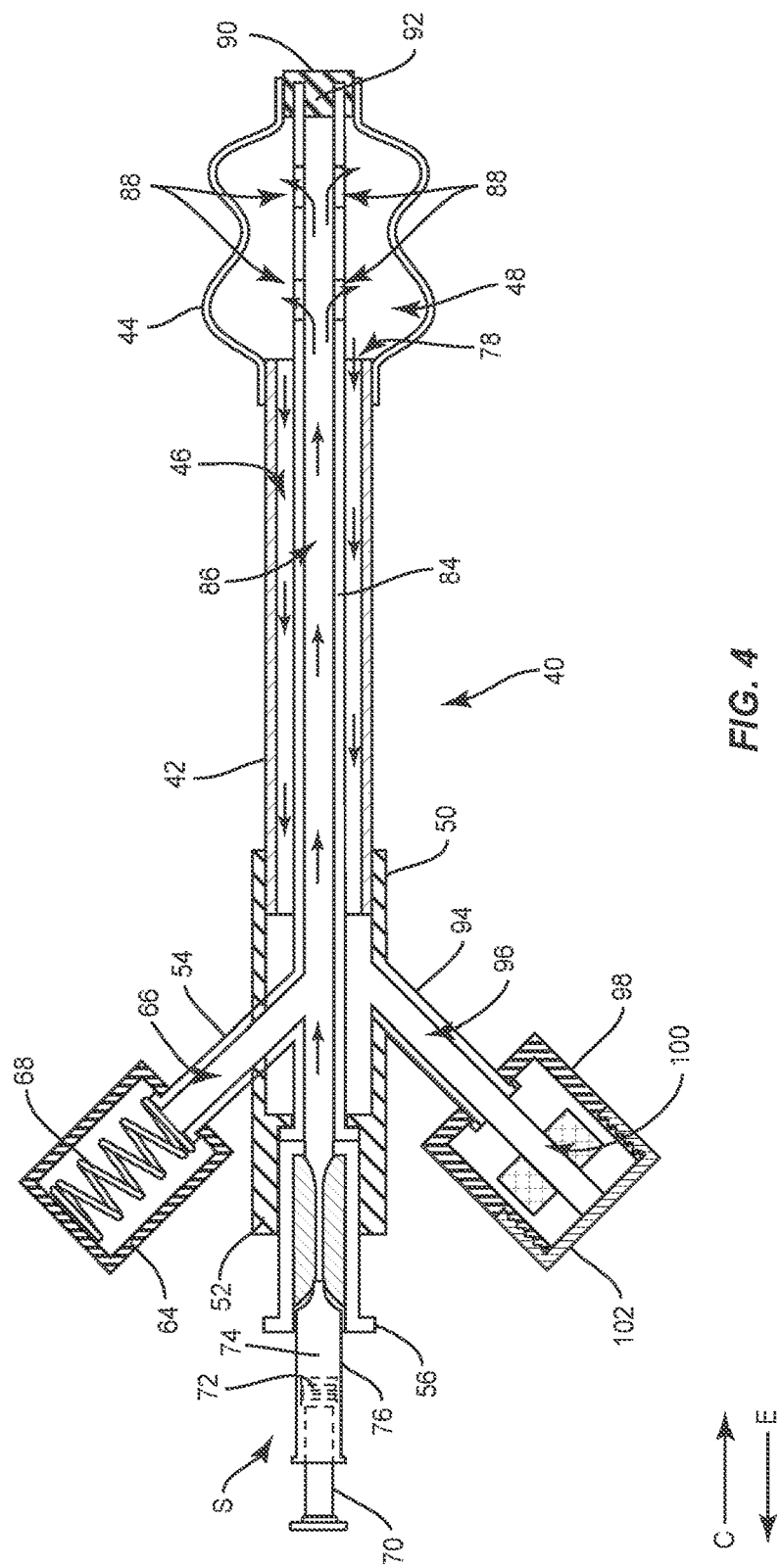
FIG. 4 is a side, cross sectional view of the surgical instrument shown in FIG. 3.
Figure 5:
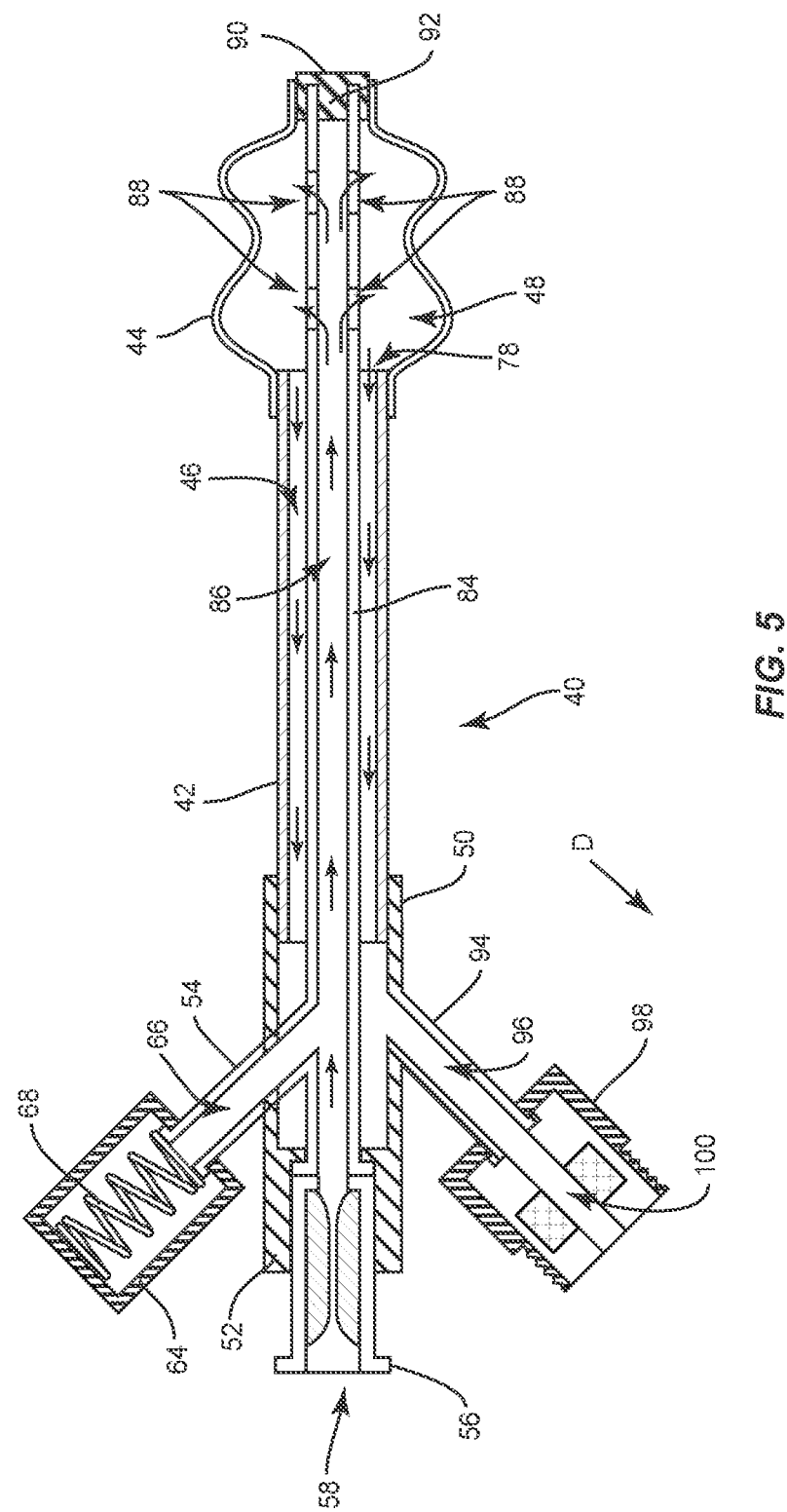
FIG. 5 is a side, cross sectional view of the surgical instrument shown in FIG. 3.

In some embodiments, balloon catheter 40 comprises a shaft, such as, for example, an inner shaft 84 positioned within cylindrical portion 42, as shown in FIGS. 3-5, for example. A distal portion of shaft 84 extends through an opening 78 of cylindrical portion 42 such that at least a portion of the distal portion of shaft 84 is positioned outside of passageway 46 of cylindrical portion 42. Proximal portion 44a of balloon 44 is coupled to a distal portion of cylindrical portion 42 and distal portion 44b of balloon 44 is coupled to shaft 84. In some embodiments, shaft 84 comprises an inner surface defining a passageway, such as, for example, a lumen 86 and one or a plurality of apertures 88 that are in communication with lumen 86 and cavity 48 of balloon 44 such that an inflation material can be moved through lumen 86 and apertures 88 and into cavity 48 to inflate balloon 44. In some embodiments, apertures 88 are spaced apart from one another radially about a circumference of inner shaft 84. In some embodiments, inner shaft 84 comprises an end wall 90 that defines a distal limit of lumen 86. In some embodiments, balloon catheter 40 comprises a plug 92 in a distal end of shaft 84 that closes lumen 86 to define a distal limit of lumen 86. In some embodiments, end wall 90 is a portion of plug 92.

Connector 50 is coupled to shaft 84 such that channel 58 of flow control device 56 is in communication with lumen 86. In some embodiments, channel 58 is coaxial with lumen 86. In the embodiments shown in FIGS. 3-5, cavity 66 of port 54 is in communication with openings in cylindrical portion 42 and shaft 84 such that cavity 66 is in communication with lumen 86. In some embodiments, cavity 66 is closed off from passageway 46 by a wall that defines cavity 66 such that cavity 66 is not in communication with passageway 46. Connector 50 includes a port 94 that is spaced apart from port 52 and from port 54. Port 94 includes a conduit 96 that is defined by a wall of port 94. Conduit 96 is in communication with an opening in cylindrical portion 42 such that conduit 96 is in communication with passageway 46. In some embodiments, conduit 96 is closed off from lumen 86 by a wall of shaft 84 that defines lumen 86 such that conduit 96 is not in communication with lumen 86. A valve, such as, for example, an EZ prep valve 98 is coupled to port 94. Valve 98 is configured for removal of inflation material from balloon catheter 40, as discussed herein. In some embodiments, valve 98 is integrally formed with port 94 such that valve 98 cannot be removed from port 94 without breaking valve 98 and/or port 94. In some embodiments, valve 98 is removable coupled to port 94. Valve 98 may be coupled to port 94 by frictional engagement, threaded engagement, mutual grooves, screws, adhesive, nails, barbs and/or raised element. Valve 98 includes a passage 100 that is in communication with conduit 96. In some embodiments, a removable cap 102 is coupled to valve 98 to close off passage 100, as shown in FIG. 3. In some embodiments, inner threads of cap 102 engage outer threads of valve 98 to couple cap 102 to valve 98. In some embodiments, cap 102 may be coupled to valve 98 by frictional engagement, threaded engagement, mutual grooves, screws, adhesive, nails, barbs and/or raised element. In some embodiments, cap 102 is a Luer cap.

In operation and use, an inflation device, such as, for example, syringe S is coupled to port 52. In some embodiments, the distal tip of syringe S is coupled to flow control device 56, as shown in FIG. 4. In some embodiments, the distal tip of syringe S includes outer threads that engage inner threads of flow control device 56 to couple syringe S to flow control device 56. Plunger 70 of syringe S is moved in direction C shown in FIG. 4 such that tip 72 of plunger 70 pushes material, such as, for example, inflation material within cavity 74 of barrel 76 of syringe S out of cavity 74. The material moves out of syringe S and through channel 58 of flow control device 56. As the material moves through channel 58, the rate of flow of the material is reduced, as discussed herein. That is, the rate of flow of the material decreases within channel 58 from the rate of flow when the material exits syringe S. The material then flows through lumen 86 and apertures 88 of shaft 84 at the reduced rate of flow and into inner cavity 48 of balloon 44 to move balloon from the uninflated configuration to the inflated configuration. As the material flows through lumen 86, spring 68 of damper 66 will compress if pressure within lumen 86 reaches a certain threshold in order to smoothen pressure peaks within lumen 86, as discussed herein. In some embodiments, the material fills all or a portion of passageway 46 as the material moves through apertures 88 and into inner cavity 48.

In some embodiments, balloon 44 is moved from the inflated configuration to the uninflated configuration by removing cap 102 from valve 98, as shown in FIG. 5. Once cap 102 is removed from valve 98, the material in passageway 46 may flow out of balloon catheter 40 through conduit 96 and passage 100 in direction D shown in FIG. 5. In some embodiments, a suction device, such as, for example, a second syringe S may be coupled to valve 98 to assist in removing the material in passageway 46 from balloon catheter 40. In some embodiments, coupled to port 52 by frictional engagement, threaded engagement, mutual grooves, screws, adhesive, nails, barbs and/or raised element. To remove the material in passageway 46 from balloon catheter 40 using second syringe S, plunger 70 of second syringe S is moved relative to barrel 76 in direction E shown in FIG. 4 such that the material in inner cavity 48 of balloon 44 is drawn through passageway 46, conduit 96 and passage 100 and into cavity 74 of syringe S. As the material exits inner cavity 48, balloon 44 moves from the inflated configuration to the uninflated configuration. In some embodiments, balloon 44 is moved from the inflated configuration to the uninflated configuration while syringe S is coupled to flow control device 56. In some embodiments, balloon 44 is moved from the inflated configuration to the uninflated configuration after syringe S is uncoupled from flow control device 56.

In use, to treat a bone disorder, such as, for example, a spinal fracture, a medical practitioner obtains access to a target location including at least one vertebra, such as, for example, a fractured vertebra, in any appropriate manner, such as through incision and retraction of tissue. It is envisioned that the balloon catheter 40 may be used in any existing surgical method or technique including open surgery, mini-open surgery, minimally invasive surgery including percutaneous surgical implantation, whereby vertebra V is accessed through a micro-incision, or sleeve that provides a protected passageway to the area. Once access to the surgical site(s) are obtained, the particular surgical procedure is performed for treating the bone disorder.

Balloon catheter 40 is moved through the incision and positioned so that balloon 44 is positioned within a vertebral body of the fractured vertebra. In some embodiments, balloon 44 is moved into the vertebral body when balloon 44 is in the uninflated configuration. The material discussed above is moved through lumen 86 such that the material flows through channel 58 and lumen 86 and into cavity 48 of balloon 44 to move balloon 44 from the uninflated configuration to the inflated configuration. As balloon 44 is gradually inflated, balloon 44 pushes cancellous bone of the vertebral body towards cortical walls of the vertebral body to form a cavity within the vertebral body. In some embodiments, balloon 44 is moved from the inflated configuration to the uninflated configuration in the manner discussed herein. Balloon catheter may then be removed from the incision. Another device may be used to fill the cavity created by balloon 44 with a material, such as, for example, bone cement.

In some embodiments, a kit containing one or more components of balloon catheter 40 is provided. The kit may comprise components from any of the embodiments discussed herein. In some embodiments, the kit comprises one or more of the inflation materials discussed herein. The kit may also comprise one or more component to assist with inserting balloon catheter 40 into a patient, such as, for example, one or a plurality of cannulas. In some embodiments, the kit comprises a plurality of cannulas having different lengths configured for use with different size patients.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. An inflatable bone tamp comprising:
    a shaft extending along an axis between a proximal end and an opposite distal end, the shaft defining a lumen, and the shaft including an outer surface, a plurality of openings therein adjacent the distal end of the shaft, and an end wall extending transverse to the axis at the distal end of the shaft;
    a cannula that surrounds the shaft between the proximal end and the distal end of the shaft, the cannula including inner surface, the inner surface of the cannula and the outer surface of the shaft defining a passageway;
    a balloon comprising a distal end engaging the distal end of the shaft, and a proximal end engaging a distal end of the cannula;
    a connector coupled to the shaft, the connector comprising a first port, a second port, and a third port, the first and second ports being in communication with the lumen, and the third port being in communication with the passageway; and
    a flow control device coupled to the first port that controls flow of a material through the first port and into the lumen; and
    a damper coupled to the second port that controls pressure within the inflatable bone tamp when pressure within the inflatable bone tamp reaches a threshold;
    wherein the material can flow from the first port, through the lumen, through the plurality of openings, and into the balloon to inflate the balloon, and the material can flow from the balloon, through the passageway, and exit the third port to deflate the balloon.

2. The inflatable bone tamp recited in claim 1, wherein the first port is positioned between the second port and the third port.

3. The inflatable bone tamp recited in claim 1, wherein the first port is coaxial with the lumen and the second and third ports each extend transverse to the lumen.

4. An inflatable bone tamp comprising:
a shaft including an inner surface, an outer surface, and a plurality of openings therein adjacent a distal end of the shaft, the inner surface of the shaft defining a lumen;
a cannula that surrounds the shaft, the cannula including an inner surface, the inner surface of the cannula and the outer surface of the shaft defining a passageway;
a balloon including an interior and being coupled to the shaft at the distal end of the shaft and coupled to the cannula at a distal end of the cannula, the lumen fluidly communicating with the interior of the balloon via the plurality of openings, and the interior of the balloon communicating with the passageway;
a connector coupled to the shaft, the connector comprising a first port, a second port, a third port, and a valve coupled to the third port, the first and second ports being in communication with the lumen;
a flow control device coupled to the first port that controls flow of a material through the first port and into the lumen; and
a damper coupled to the second port that controls pressure within the inflatable bone tamp when pressure within the inflatable bone tamp reaches a threshold;
wherein the material can flow through the lumen, through the plurality of openings, and into the interior of the balloon to inflate the balloon, and flow from the interior of the balloon through the passageway to deflate the balloon, and
wherein the valve is configured for removal of the material from the passageway through the third port to facilitate deflation of the balloon.

5. The inflatable bone tamp recited in claim 1, wherein the flow control device comprises a tapered channel.

6. The inflatable bone tamp recited in claim 1, wherein the flow control device comprises a channel that is tapered from a proximal end of the flow control device to a distal end of the flow control device.

7. The inflatable bone tamp recited in claim 1, wherein the flow control device comprises a channel that is tapered from a proximal end of the flow control device to a midpoint of the flow control device and from a distal end of the flow control device to the midpoint.

8. The inflatable bone tamp recited in claim 1, wherein the flow control device comprises a tapered channel that is coaxial with the lumen.

9. The inflatable bone tamp recited in claim 1, wherein a proximal end of the balloon is coupled to the distal end of the cannula and a distal end of the balloon is coupled to the distal end of the shaft.

10. The inflatable bone tamp recited in claim 1, wherein the material from the lumen moves through the second port and into the damper.

11. The inflatable bone tamp recited in claim 1, wherein the valve comprises a removable cap that is positioned over a portion of the valve when the balloon is being inflated and is removed from the portion of the valve when the balloon is being deflated.

12. The inflatable bone tamp recited in claim 11, wherein the removable cap is a Luer cap.

13. The inflatable bone tamp recited in claim 1, wherein the damper is a check valve.

14. The inflatable bone tamp recited in claim 1, wherein the damper comprises a spring that compresses when pressure within the inflatable bone tamp reaches the threshold.

15. The inflatable bone tamp recited in claim 1, wherein the shaft is a polymer tube.

16. The inflatable bone tamp recited in claim 1, wherein the first port is positioned between the second port and the third port.

17. The inflatable bone tamp recited in claim 1, wherein the first port is coaxial with the lumen and the second and third ports each extend transverse to the lumen.

18. The inflatable bone tamp recited in claim 1, wherein the flow control device is coupled to the first port such that a channel of the flow control device is in communication with the lumen.

19. An inflatable bone tamp comprising:
a shaft including an inner surface, an outer surface, and a plurality of openings therein adjacent a distal end of the shaft, the inner surface of the shaft defining a lumen;
a cannula that surrounds the shaft, the cannula including an inner surface, the inner surface of the cannula and the outer surface of the shaft defining a passageway that is in communication with the lumen;
a balloon having a proximal end that is coupled to the cannula and a distal end that is coupled to the shaft such that a material can flow through the lumen, through the plurality of openings, and into the balloon to facilitate inflation of the balloon, and the material can flow from the balloon, and through the passageway to facilitate deflation of the balloon;
a connector coupled to the shaft, the connector comprising a first port, a second port, and a third port, the ports each being in communication with one of the lumen and the passageway;
a flow control device comprising a tapered channel, the flow control device being coupled to the first port to control flow of the material through the tapered channel and into the lumen;
a damper coupled to the second port that controls pressure within the inflatable bone tamp when pressure within the inflatable bone tamp reaches a threshold; and
a valve coupled to the third port, the valve being configured for removal of the material from the inflatable bone tamp through the third port to deflate the balloon.

20. The inflatable bone tamp recited in claim 19, wherein the proximal end of the balloon is coupled to a distal end of the cannula and the distal end of the balloon is coupled to the distal end of the shaft.

* * * * *